United States Patent
Cho et al.

(10) Patent No.: US 10,368,845 B2
(45) Date of Patent: Aug. 6, 2019

(54) ULTRASONIC PROBE

(71) Applicant: SAMSUNG ELECTRONICS CO., LTD., Suwon-si (KR)

(72) Inventors: Kyungil Cho, Seoul (KR); Jong Keun Song, Yongin-si (KR); Seungheun Lee, Seongnam-si (KR); Baehyung Kim, Yongin-si (KR); Youngil Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 546 days.

(21) Appl. No.: 14/613,769

(22) Filed: Feb. 4, 2015

(65) Prior Publication Data

US 2015/0289852 A1     Oct. 15, 2015

(30) Foreign Application Priority Data

Apr. 14, 2014  (KR) .................. 10-2014-0044454

(51) Int. Cl.
*A61B 8/00*     (2006.01)

(52) U.S. Cl.
CPC ............. *A61B 8/546* (2013.01); *A61B 8/44* (2013.01); *A61B 8/4444* (2013.01)

(58) Field of Classification Search
CPC ......... A61B 8/546; A61B 8/44; A61B 8/4444; A61B 8/00

See application file for complete search history.

(56) References Cited

U.S. PATENT DOCUMENTS

| | | | |
|---|---|---|---|
| 5,560,362 A * | 10/1996 | Sliwa, Jr. | A61B 8/546 600/439 |
| 2006/0173344 A1* | 8/2006 | Marian | A61B 8/00 600/459 |
| 2008/0188755 A1 | 8/2008 | Hart | |
| 2010/0022882 A1* | 1/2010 | Duckworth | A61B 5/6805 600/447 |
| 2011/0282211 A1 | 11/2011 | Shikata | |
| 2013/0286593 A1 | 10/2013 | Cho et al. | |

(Continued)

FOREIGN PATENT DOCUMENTS

| CN | 1897877 A | 1/2007 |
|---|---|---|
| CN | 103371851 A | 10/2013 |

(Continued)

OTHER PUBLICATIONS

Communication dated Feb. 13, 2017, issued by the European Patent Office in counterpart European Application No. 15163301.3.

(Continued)

*Primary Examiner* — Joel Lamprecht
(74) *Attorney, Agent, or Firm* — Sughrue Mion, PLLC

(57) ABSTRACT

Disclosed herein is an ultrasonic probe configured to release heat generated by a transducer to an exterior of the ultrasonic probe via a heat pipe and a radiator. The ultrasonic probe includes a housing; a transducer configured to generate ultrasonic waves while disposed in an interior of the housing; a heat pipe configured to transfer the heat generated by the transducer; a radiator connected to the heat pipe and configured to release the heat, which is transferred via the heat pipe, to the exterior of the housing; and a partition wall configured to separate an inside space within the housing.

18 Claims, 10 Drawing Sheets

(56) References Cited

U.S. PATENT DOCUMENTS

2014/0360274 A1    12/2014    Cho et al.
2014/0364742 A1    12/2014    Cho et al.

FOREIGN PATENT DOCUMENTS

| CN | 103429161 A | 12/2013 |
|---|---|---|
| JP | 58-2666 U | 1/1983 |
| JP | 1-80107 U | 5/1989 |
| JP | 2007209699 A | 8/2007 |
| JP | 2008284003 A | 11/2008 |
| JP | 2009160068 A | 7/2009 |
| JP | 2009165509 A | 7/2009 |
| JP | 2010-88610 A | 4/2010 |

OTHER PUBLICATIONS

Communication dated Aug. 28, 2015 issued by the European Patent Office in counterpart Application No. 15163301.3.
Communication dated Nov. 16, 2017, issued by the European Patent Office in counterpart European Application No. 15163301.3.
Communication issued Aug. 21, 2018, issued by the Japanese Patent Office in counterpart Japanese Patent Application No. 2015-022275.
Office Action issued Jan. 4, 2019 by the State Intellectual Property Office of p.R. China in counterpart Chinese Patent Application No. 201510162239.3.
Communication dated Mar. 26, 2019, from the Japanese Patent Office in counterpart application No. 2015-022275.

* cited by examiner

ULTRASONIC PROBE

CROSS-REFERENCE TO RELATED APPLICATION

This application claims priority from Korean Patent Application No. 10-2014-0044454, filed on Apr. 14, 2014, in the Korean Intellectual Property Office, the disclosure of which is incorporated herein by reference in its entirety.

BACKGROUND

1. Field

Exemplary embodiments relate to an ultrasonic probe of an ultrasonic diagnosis apparatus configured to diagnose diseases.

2. Description of the Related Art

An ultrasonic diagnosis apparatus is an apparatus configured to radiate ultrasonic waves toward a target portion at an inside of a subject, and to obtain an image with respect to a cross section of a blood flow of a soft tissue by receiving reflected ultrasonic echo signals.

The ultrasonic diagnosis apparatus, when compared to other image diagnosis apparatuses such as an x-ray apparatus, a CT Scanner (Computerized Tomography Scanner), a MRI (Magnetic Resonance Image), and a nuclear diagnosis apparatus, is provided in a relatively small size and is generally less expensive, while being capable of displaying diagnostic images in real time. In addition, the level of safety of the ultrasonic diagnosis apparatus is relatively high, as no radiation exposure is present, and thus, as well as for gynecological diagnoses, the ultrasonic diagnosis apparatus is being widely used for diagnosis of hearts, abdomens, and urinary systems.

The ultrasonic diagnosis apparatus includes an ultrasonic probe configured to irradiate ultrasonic waves toward a subject so as to obtain images of an inside of the subject, and to obtain ultrasonic echo signals that are reflected from body parts of the subject.

In general, piezo-electric material, which is configured to generate ultrasonic waves by converting electrical energy into mechanical vibrational energy, is being widely used as a transducer that is configured to generate ultrasonic waves at the ultrasonic probe.

Recently, a cMUT (capacitive Micromachined Ultrasonic Transducer), a new-concept transducer, is being developed.

The cMUT, as a new-concept transducer configured to transmit and/or receive ultrasonic waves by use of vibrations of hundreds or thousands of micromachined thin films, is manufactured on the basis of the MEMS (Micro Electro Mechanical System) technology. After forming a lower electrode and an air gap at a board of a semiconductor being used in a general semiconductor process and then forming an air gap at an upper portion of an insulating layer having the lower electrode, when a thin film provided with a thickness of about several to thousands of angstroms as well as an upper electrode above the air gap, a capacitor is formed so as to be provided with the air gap therebetween.

When an alternating current is applied to the capacitor manufactured as described above, the thin films are vibrated, and ultrasonic waves are formed as a result. Conversely, in a case when the thin films are vibrated by outside ultrasonic waves, the capacitance of the capacitor is changed, and by detecting the change of the capacitance, the ultrasonic waves are received.

The cMUT as such is provided with a diameter thereof which is on the order of about tens of micrometers, and thus, even in a case when tens of thousands of the cMUTs are arranged, the size thereof may be only about several millimeters. In addition, through a single manufacturing process, tens of thousands of sensors may be able to be precisely and simultaneously arranged at desired positions, and since the cMUT element is connected to an ASIC as a result of a chip-bonding method, such as in flip-chip bonding, so as to apply electrical signals to the cMUT, the difficulty with respect to the degree of complexity of the process caused by conventional wirings may be solved.

The cMUT as such may be suitable for the manufacturing of 2D-array transducers, which is a recent trend, thereby contributing the development of multi-channel transducers.

When the number of transducer channels is low, the heat generated from electrical circuits provided as to drive a probe may be less than about 1 W, which is the level that may be naturally released through a probe case. However, as transducers are provided with multiple channels, the amount of heat generated therefrom may be increased up to the level of about 7 W, and therefore, the technological development to radiate and reduce heat from the ultrasonic probe is in demand.

SUMMARY

Therefore, it is an aspect of one or more exemplary embodiments to provide an ultrasonic probe configured to release heat generated by a transducer to an outside of the ultrasonic probe via a heat pipe and a radiation unit.

Additional aspects of the exemplary embodiments will be set forth in part in the description which follows and, in part, will be obvious from the description, or may be learned by practice of the exemplary embodiments.

In accordance with one exemplary embodiment, an ultrasonic probe includes a housing, a transducer, a heat pipe, a radiator, and a partition wall. The transducer may be configured to generate ultrasonic waves while disposed in an interior of the housing. The heat pipe may be configured to facilitate a transfer of heat generated by the transducer. The radiator may be connected to the heat pipe and configured to release the heat being transferred via the heat pipe to an exterior of the housing. The partition wall may separate an inside space within the housing.

The ultrasonic probe may further include an electrical apparatus provided in the interior of the housing, and the partition wall may separate a first space in which the electrical apparatus is provided from a second space in which the radiator is provided.

The ultrasonic probe may further include: a cable electrically connected to the electrical apparatus; and a cable extender provided at a rear portion of the housing as to extend the cable to the exterior of the housing, wherein the cable extender may be positioned so as not to interfere with the radiator and so as not to interfere with the heat pipe.

The heat pipe may be further configured to facilitate the transfer of the heat generated by the transducer in a first direction which differs from a radiation direction of the generated ultrasonic waves by at least 90 degrees.

A vent hole configured to facilitate a passage of air therethrough may be provided at the housing and may be further configured to cover the radiator.

The radiator may further include a radiation fin configured to scatter the heat transferred via the heat pipe.

The ultrasonic probe may further include a radiation fan configured to release the heat scattered by the radiation fin to the exterior of the housing.

In accordance with another exemplary embodiment, an ultrasonic probe includes a housing, a transducer, a heat pipe, and a radiator. The transducer may be configured to generate ultrasonic waves while disposed in an interior of the housing. The heat pipe may be configured to facilitate a transfer of heat generated by the transducer. The radiator may be connected to the heat pipe and configured to release the heat being transferred via the heat pipe to an exterior of the housing. The radiator may be positioned such that an inside space within the housing is divided.

The ultrasonic probe may further include an electrical apparatus provided in the interior of the housing, wherein the radiator may positioned so as to isolate a space in which the electrical apparatus is provided.

The ultrasonic probe may further include a cable electrically connected to the electrical apparatus, and a cable extender provided at a rear portion of the housing as to extend the cable to the exterior of the housing. The cable extender may be positioned so as not to interfere with the radiator and so as not to interfere with the heat pipe.

The radiator may be provided with a shape thereof which corresponds to a shape of the housing.

In accordance with another exemplary embodiment, an ultrasonic probe includes a first housing, a transducer, a heat pipe and a second housing. The transducer may be configured to generate ultrasonic waves while disposed in an interior of the first housing. The heat pipe may be configured to facilitate a transfer of heat generated by the transducer. The second housing may be connected to the heat pipe and configured to release the heat being transferred via the heat pipe to an exterior of the second housing.

The second housing may be formed of at least one from among aluminum, copper, and an alloy of aluminum and copper.

The ultrasonic probe may further include an electrical apparatus, a cable electrically connected to the electrical apparatus, and a cable extender provided at a rear portion of the second housing such that the cable is extended to an exterior of the second housing. The cable extender may be positioned such that the cable does not interfere with the heat pipe.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
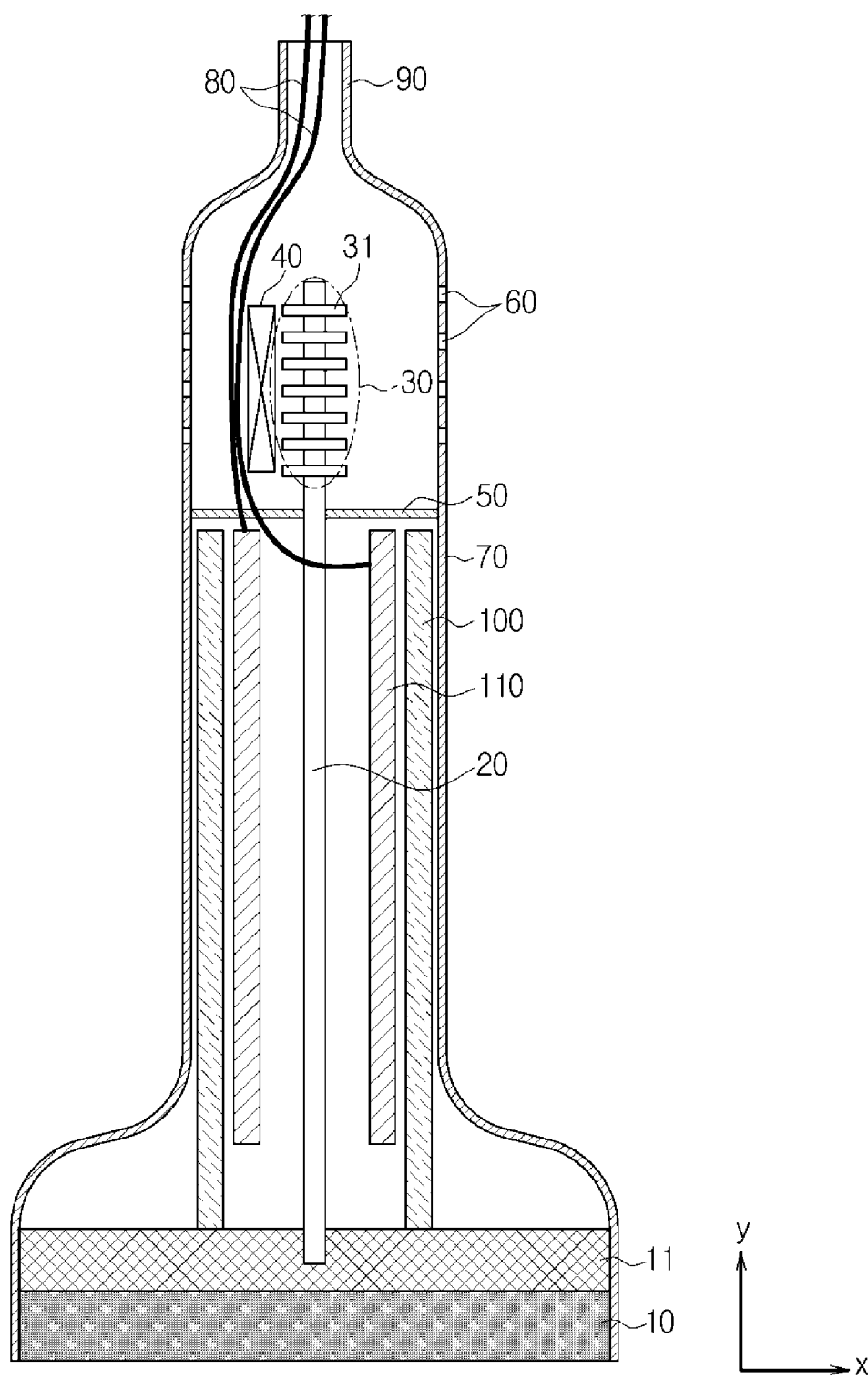
FIG. 1 is a drawing schematically showing a structure of one exemplary embodiment of an ultrasonic probe.

Reference will now be made in detail to exemplary embodiments, examples of which are illustrated in the accompanying drawings, wherein like reference numerals refer to like elements throughout.

Figure 2:
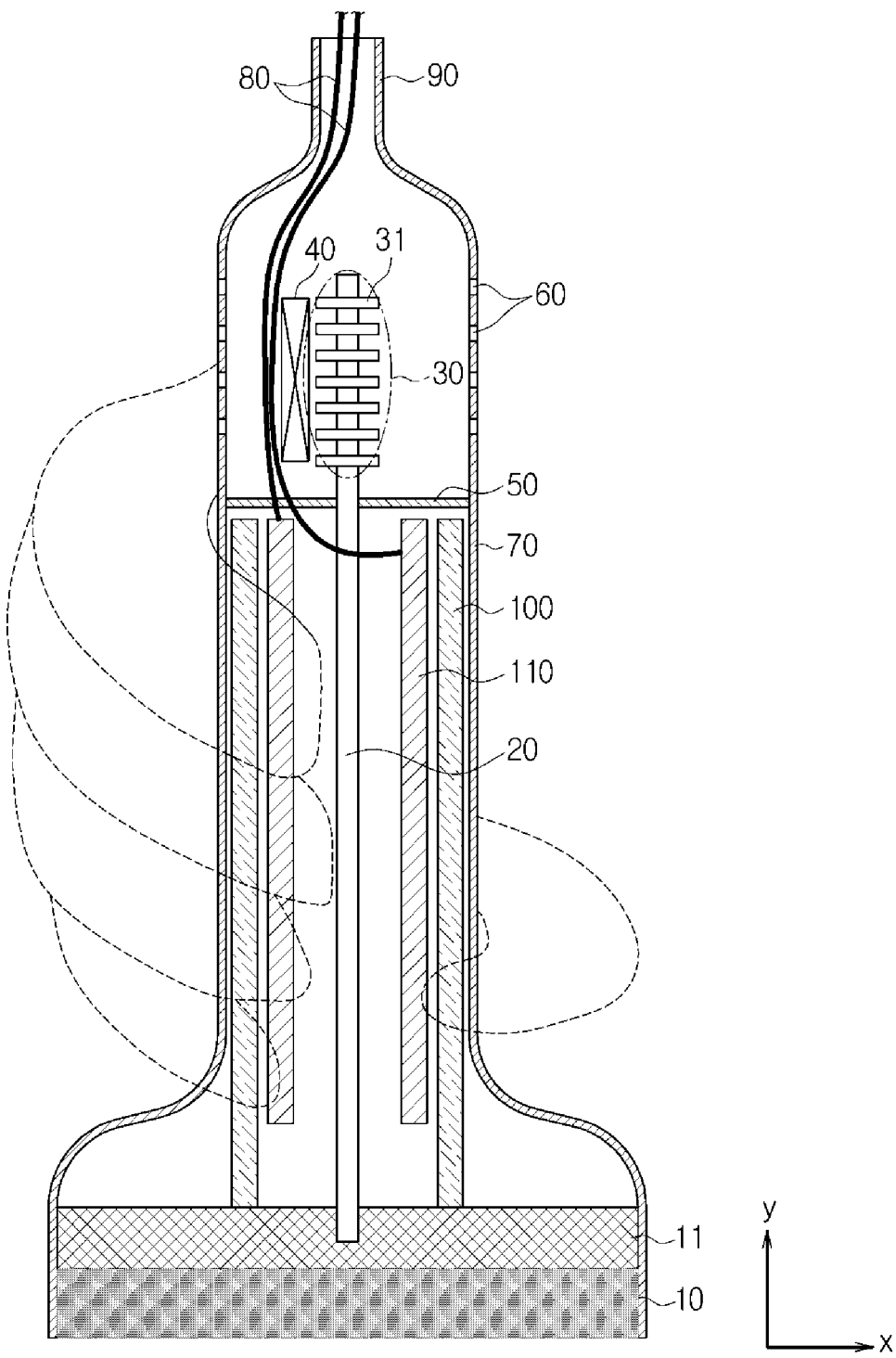
FIG. 2 is a drawing illustrating an image of the ultrasonic probe of FIG. 1 being gripped.
Figure 3:
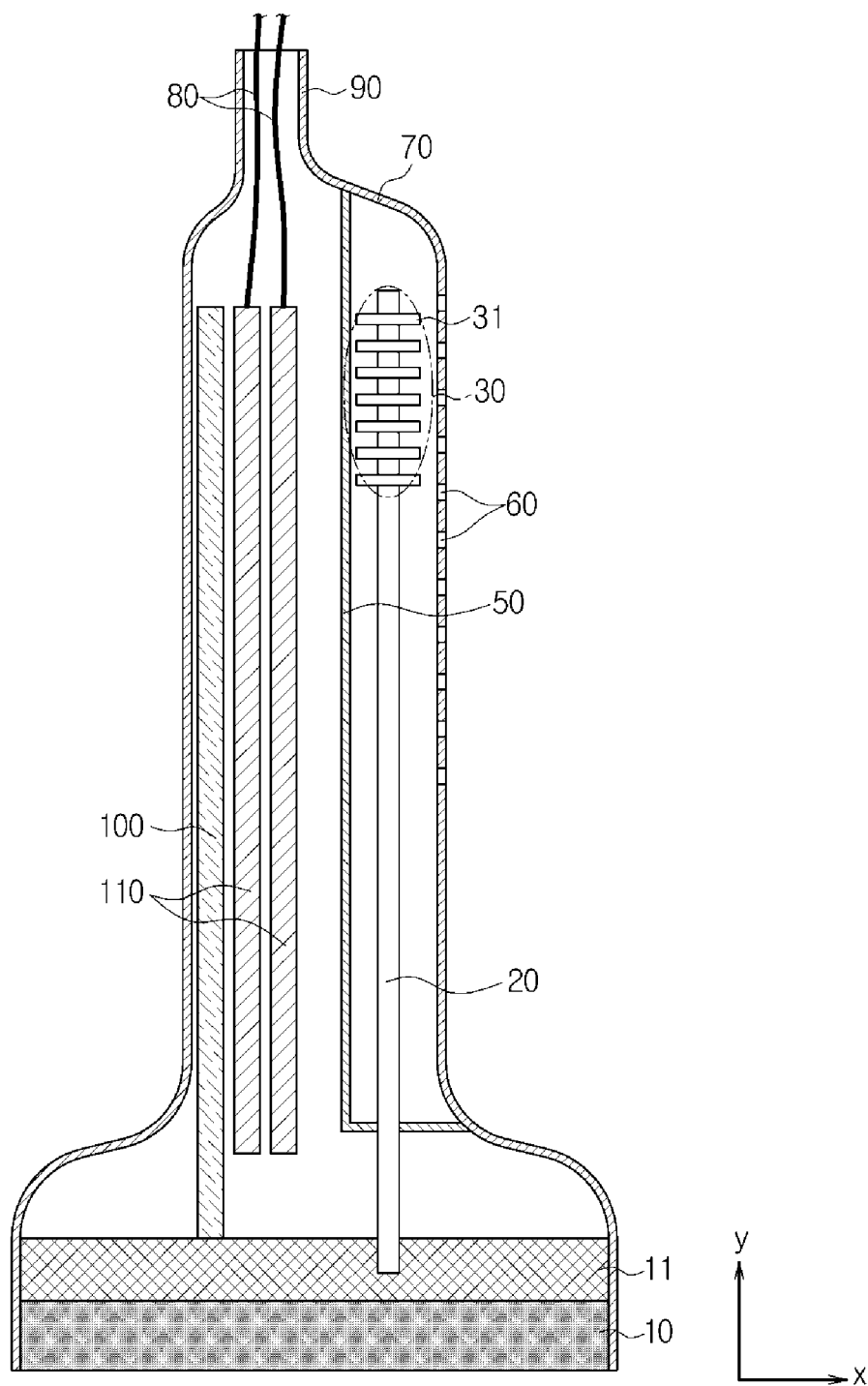
FIG. 3 is a drawing schematically showing an alternative structure according to another exemplary embodiment of the ultrasonic probe.
Figure 4:
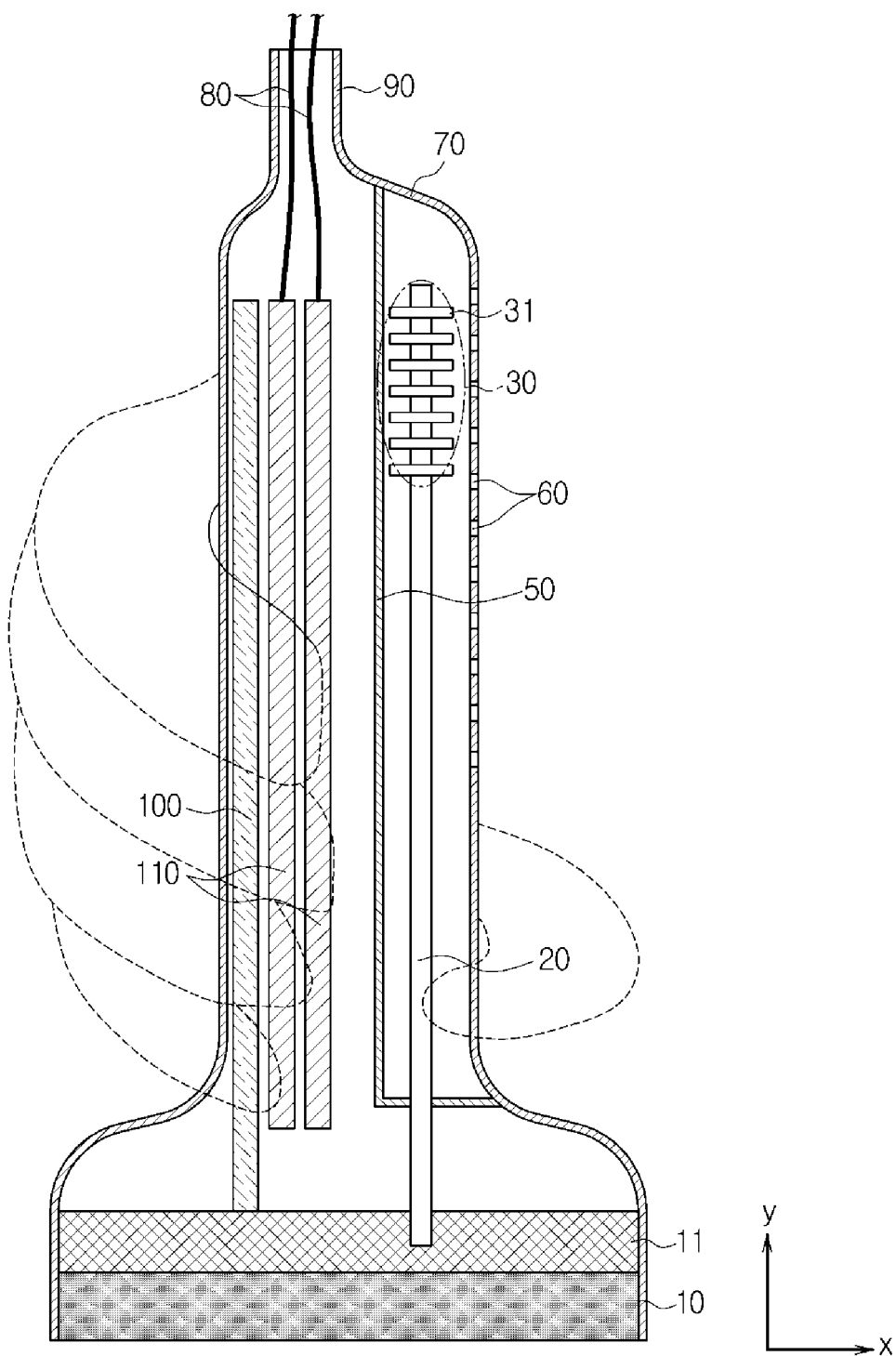
FIG. 4 is a drawing illustrating an image of the ultrasonic probe of FIG. 3 being gripped.

FIG. 1 is a drawing schematically showing a structure of an exemplary embodiment of an ultrasonic probe, and FIG. 2 is a drawing illustrating an image of the ultrasonic probe of FIG. 1 being gripped. FIG. 3 is a drawing showing a partially changed structure of the ultrasonic probe illustrated in FIG. 1, and FIG. 4 is a drawing illustrating an image of the ultrasonic probe of FIG. 3 being gripped.

Referring to FIG. 1, FIG. 2, FIG. 3, and FIG. 4, an ultrasonic probe includes a transducer 10, a heat pipe 20 to facilitate a transfer of the heat generated by the transducer 10, and a radiation unit (also referred to herein as a "radiator") 30 to release the heat transferred via the heat pipe 20 to an exterior of the ultrasonic probe.

With respect to one exemplary embodiment of the transducer 10, a Magnetostrictive Ultrasonic Transducer, which is configured to use a magnetostrictive effect of a magnetic substance that is typically used in conjunction with a conventional probe apparatus, or a Piezoelectric Ultrasonic Transducer, which is configured to use a piezoelectric effect of a piezoelectric substance, may be used. Alternatively, a Capacitive Micromachined Ultrasonic Transducer, hereinafter referred to as a cMUT, configured to transmit/receive ultrasonic waves by use of vibrations of hundreds or thousands of micromachined thin films, may be also used.

The heat pipe 20 is configured to facilitate the transfer of the heat generated at the transducer 10 in a y-axis direction, that is, a direction opposite to a radiating direction of ultrasonic waves.

Figure 5:
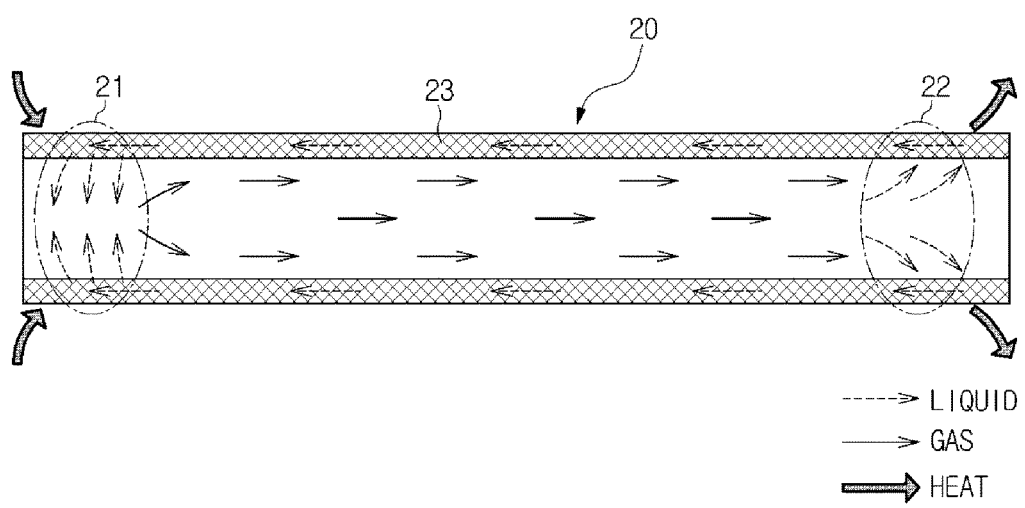
FIG. 5 is a drawing illustrating an operation principle of a heat pipe.

FIG. 5 is a drawing illustrating an operational principle of the heat pipe 20.

The heat pipe 20 is an apparatus which is manufactured by injecting working fluid into a sealed container having the shape of a tube and provided to be in a vacuum state.

The working fluid within the heat pipe 20 is configured to transfer heat while being present in two phases.

Referring to FIG. 5, when heat is applied to an evaporation unit (also referred to herein as an "evaporator") 21 of the heat pipe 20, the heat is transferred to an interior of the heat pipe 20 by heat conductivity through an outer wall.

An evaporation of the working fluid occurs at a surface of a wick 22 even at a low temperature in the interior of the heat pipe 20, which is provided with a high pressure.

Density and pressure of gas are increased at the evaporation unit 21 due to the evaporation of the working fluid, and thus, at a central portion, a gradation of the pressure is formed at a gas flow path toward a direction of a condensation unit (also referred to herein as a "condenser") 22 at which density and pressure of the gas are relatively lower, and as a result, the gas is moved.

At this time, the gas being moved carries an amount of heat which is equivalent to an amount of the latent heat that is evaporated.

Heat is released as the gas which is moved to the condensation unit 22 is condensed at an inner wall of the condensation unit, which is provided with a relatively lower temperature, and then the gas is returned to a liquid state.

The working fluid that is returned to the liquid state is moved again toward the evaporation unit 21 through air pores at an interior of the wick 22 by a capillary force of the wick 22 or by a gravitational force.

As the processes as described above are repeated, the transfer of heat continuously takes place.

The evaporation unit 21 of the heat pipe 20 is installed such that the evaporation unit 21 is in contact with a heat spreader 11 that is configured to absorb the heat which is generated at the transducer 10, and the heat pipe 10 is configured to transfer the heat generated at the transducer 10 to a rear portion of the ultrasonic probe by performance of the heat transfer processes that are described above.

The heat spreader 11 may be formed with a metallic material having a relatively high heat conductivity, such as aluminum. The heat spreader 11 thermally contacts with respect to the transducer 10 at which heat is generated, and is configured to absorb the heat that is generated at the transducer 10.

The heat pipe 20 is configured to make contact with respect to the heat spreader 11 while inserted into the heat spreader 11 by a predetermined depth so as to effectively facilitate a transfer of the heat absorbed by the heat spreader 11.

The heat transferred through the heat pipe 20 is released to an exterior of the ultrasonic probe through the radiation unit 30 which is provided at the condensation unit 22 of the heat pipe 20.

Referring to FIG. 1, the radiation unit 30 includes a plurality of fins 31 which have the shape of a panel while formed with metallic material so as to scatter the heat transferred from the heat pipe 20.

The condensation unit 22 of the heat pipe 20 is configured to make contact with respect to the fins 31 of the radiation unit 30, and when heat is released as the gas being moved to the condensation unit 22 is condensed at an inner wall of the condensation unit 22 at which the temperature is relatively low, the heat that is released from the condensation unit 22 of the heat pipe 20 is scattered by the fins 31.

A radiation fan 40 may be adjacently provided at the radiation unit 30. The radiation fan 40 is configured to release the heat, which is scattered by the radiation fins 31, to the exterior so as to additionally enhance radiation performance.

A housing 70 is provided so as to form a case of the ultrasonic probe, and as illustrated on FIG. 1, a plurality of vent holes 60 through which air may pass may be formed at the housing 70 so as to cover the space in which the radiation unit 30 is provided.

The heat being released from the radiation unit 30 may be discharged to the outside as a result of ventilations of air through the vent holes 60.

In a case when the radiation fan 40 is mounted, the radiation fan 40 may be able to assist so as to increase an effectiveness of the discharging of heat by generating a forced current.

As the vent holes 60 are formed, outside air may be drawn in to an interior of the housing 70 through the vent holes 60, and at this time, dust or foreign substance may also be drawn in through the vent holes 60.

The drawing in of the dust or the foreign substance as such may negatively affect an electrical apparatus 110, such as a printed circuit board provided at an interior of the ultrasonic probe, and thus, as illustrated on FIG. 1, by installing a partition wall 50 in an interior of the housing 70, the space in which the electrical apparatus 110 is situated may be isolated, so that the difficulty as such may be solved.

The vent holes 60 are formed at a portion of the housing 70 which is adjacent to the radiation unit 30, and thus, the partition wall 50 is provided at a position so to separate the radiation unit 30 from the electrical apparatus 110.

The radiation unit 30 is separated from the electrical apparatus 110 by the partition wall 50, and a cable 80 configured to apply electrical signals to the heat pipe 20 and the electrical apparatus 110 and/or to receive electrical signals from the electrical apparatus 110 is provided so as to penetrate the partition wall 50.

As illustrated in FIG. 1, the cable 80 electrically connected to the electrical apparatus 110 is extended to an exterior of the ultrasonic probe through a cable extension unit (also referred to herein as a "cable extender" 90 which is provided at the rear end of the ultrasonic probe.

On FIG. 1, the cable extension unit 90 is provided at a central portion of the rear end of the ultrasonic probe, but the cable extension unit 90 may be eccentrically provided at the rear end of the ultrasonic probe such that the cable 80 may be prevented from interfering with respect to the heat pipe 20 and/or the radiation unit 30. The above may be confirmed at the ultrasonic probe illustrated on FIG. 2.

In this aspect, the portion at which the transducer 10 is provided is defined as the front end of the heat spreader 11, and the opposite side, that is, the portion at which the cable extension unit 90 is provided, is defined as the rear end of the ultrasonic probe.

In FIG. 1, for additional enhancement of radiation performance, a radiation fin 100 provided so as to make contact with respect to the heat spreader 11 and configured to release the heat absorbed at the heat spreader 11 may be provided.

As illustrated in FIG. 1, the two units of the radiation fin 100 may be adjacently provided at an inner side surface of the housing 70, and the radiation fin 100 may be formed with a metallic material which has a relatively high heat conductivity, such as, for example, aluminum.

The radiation fin 100 is configured to release the heat absorbed at the heat spreader 11 by use of heat conductivity through the housing 70 to an exterior of the housing 70. In general, as the heat conductivity of the radiation fin 100 is larger than the heat conductivity of the housing 70 and as the heat conductivity of the housing 70 is larger than the heat conductivity of outside air, the heat of the radiation fin 100 is transferred and released to the exterior of the housing 70 by means of heat conductivity through the housing 70.

On FIG. 2, an image of the ultrasonic probe illustrated in FIG. 1 being grabbed by use of a hand is illustrated. The shape of the hand grabbing the ultrasonic probe is illustrated with dotted lines.

As illustrated in FIG. 2, a user of the ultrasonic probe may be able to grab the ultrasonic probe so as to avoid covering a portion at which the vent holes 60 are formed as to further efficiently release heat, and the shape of the housing may be designed as to facilitate the grabbing as such.

The ultrasonic probe shown in FIG. 3 is referred to as an alternative exemplary embodiment with respect to the ultrasonic probe illustrated on FIG. 1, and the heat pipe 20 is connected to an area that is off-center with respect to the central portion of the heat spreader 11.

On FIG. 1, the vent holes 60 are formed at the rear end portion of the housing 70 in an area which is adjacent to the radiation unit 30, while in FIG. 3, the heat pipe 20 is eccentrically installed with respect to the heat spreader 11, and thus, the vent holes 60 are formed only at one portion of surface of the housing 70, that is, at a portion of the housing 70 that is adjacent to the radiation unit 30.

In particular, on FIG. 1, the vent holes 60 are formed at the rear end of the housing 70, and on FIG. 3, the vent holes 60 are formed in vertical directions from one side surface of the housing 70.

As described above, when air is drawn in through the vent holes 60, outside dust or foreign substance may also be drawn in, and the outside dust or the foreign substance may negatively affect the electrical apparatus 110, and thus, similarly as in FIG. 1, the partition wall 50 is installed in an interior of the housing 70.

The partition wall 50 is provided so as to protect the electrical apparatus 110 from the dust or foreign substance which is drawn in from an outside, and as illustrated on FIG. 3, the partition wall 50 may be formed along the y-axis direction.

The radiation unit 30 and the electrical apparatus 110 are separated from one another by the partition wall 50, while the heat pipe 20 is provided so as to penetrate a portion of the partition wall 50.

As the heat pipe 20 is eccentrically installed, as illustrated in FIG. 3, the electrical apparatus 110 and/or the radiation fin 100 may be eccentrically provided at an opposite domain with respect to the domain at which the heat pipe 20 is installed.

Thus, the cable extension unit 90 at which the cable 80 is extended to an outside is eccentrically provided at the rear end of the ultrasonic probe as well, and subsequently, the cable 80 may be prevented from interfering with respect to the heat pipe 20 and the radiation unit 30.

Figure 6:
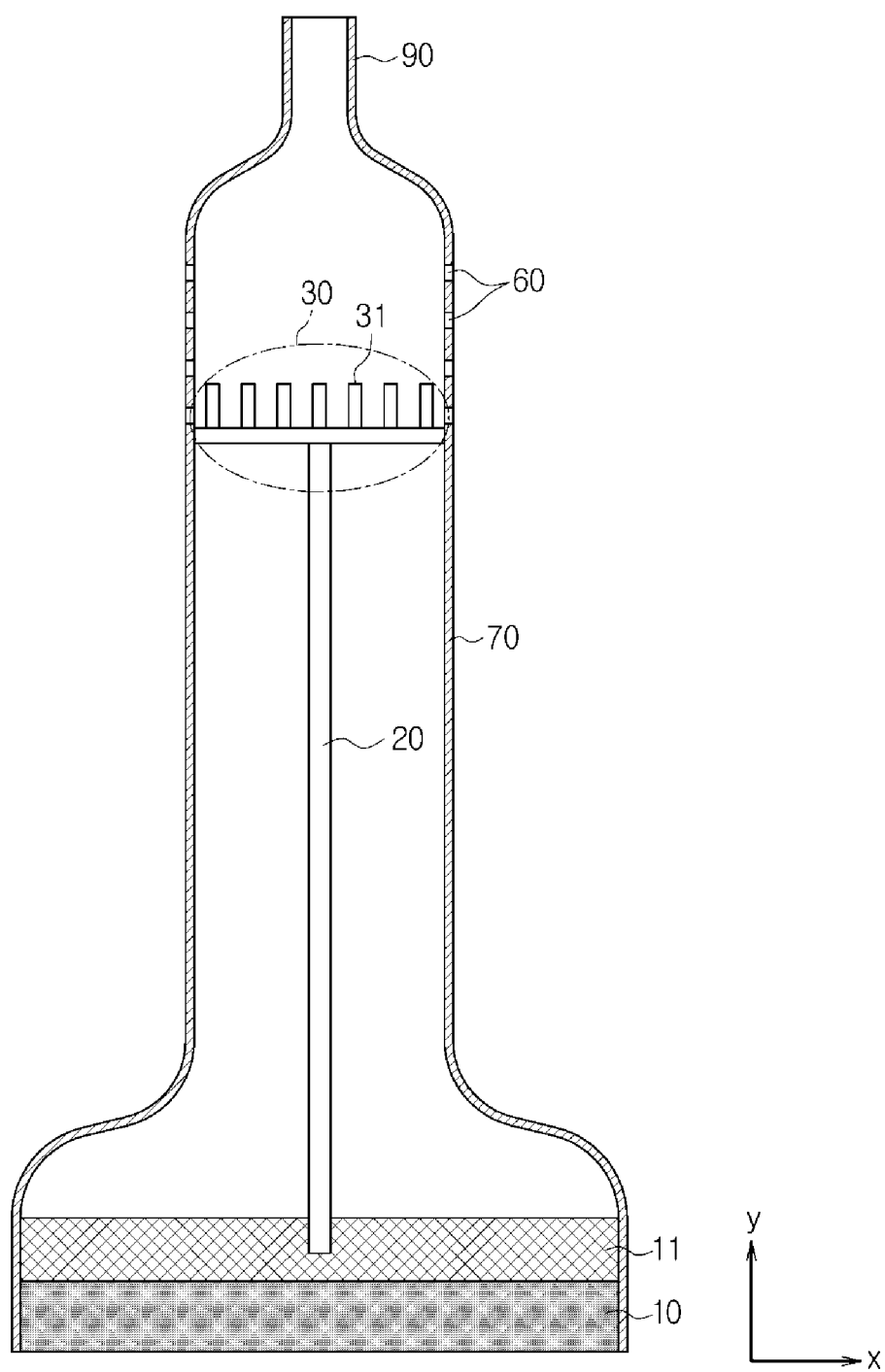
FIGS. 6, 7, and 8 are drawings schematically illustrating a structure of another exemplary embodiment of the ultrasonic probe.
Figure 7:
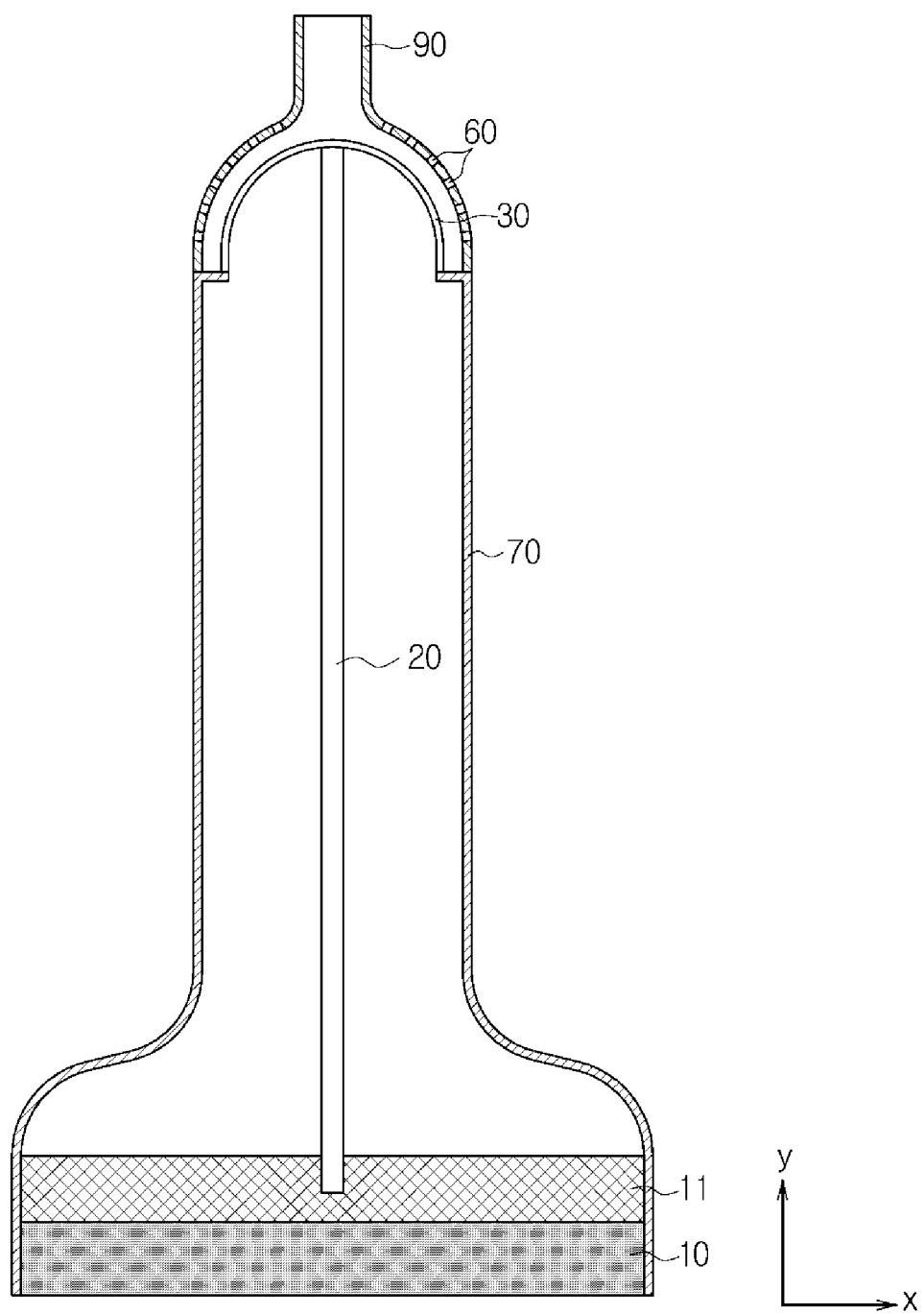
Figure 8:
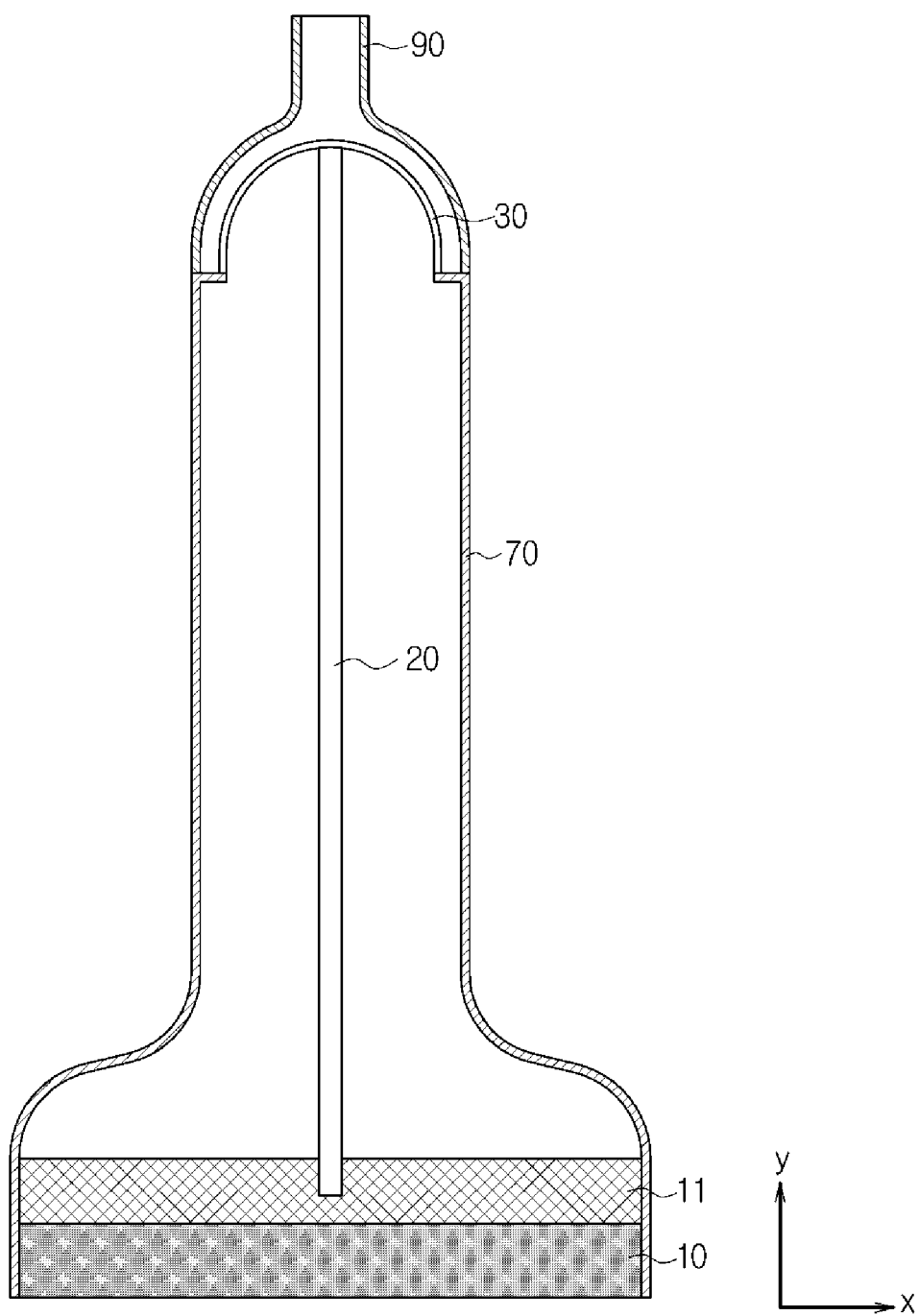
Figure 9:
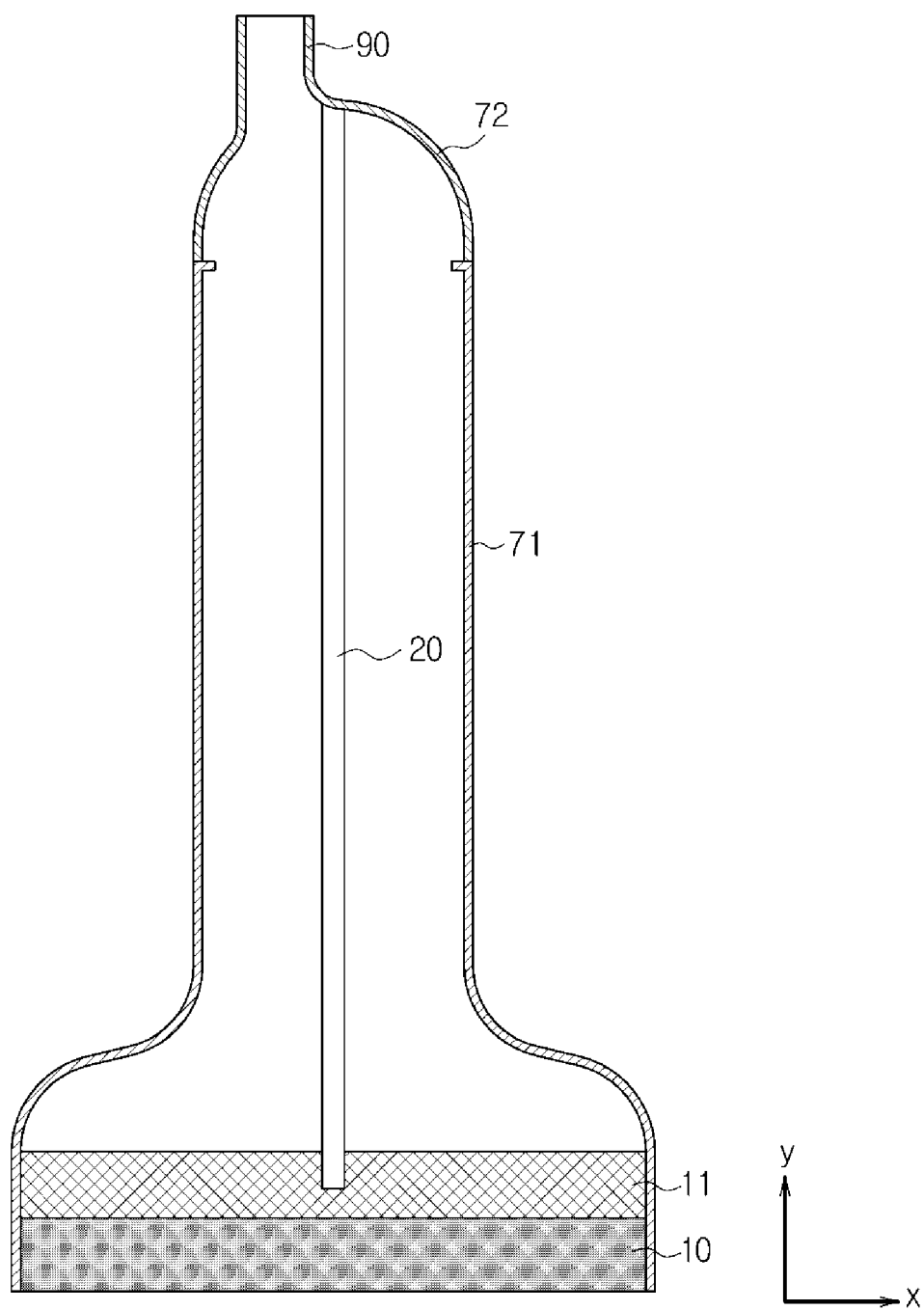
FIG. 9 is a drawing schematically illustrating a structure of still another exemplary embodiment of the ultrasonic probe.

FIG. 6 is a drawing schematically illustrating a structure of another exemplary embodiment of the ultrasonic probe, and FIG. 7 and FIG. 8 are drawings schematically showing respective alternative structures of the ultrasonic probe illustrated on FIG. 6. FIG. 9 is a drawing schematically illustrating a structure of still another exemplary embodiment of the ultrasonic probe.

FIG. 6, FIG. 7, FIG. 8, and FIG. 9 are provided as to illustrate the heat pipe 20 and the radiation unit 30 as primary structures while omitting other structures other than the heat pipe 20 and the radiation unit 30 by comparison with the structures of the ultrasonic probe illustrated in FIG. 1, FIG. 2, FIG. 3, and FIG. 4.

With respect to the difference between the ultrasonic probe shown on FIG. 6 and the ultrasonic probe shown on FIG. 1, the partition wall 50 configured to separate the electrical apparatus 110 and the radiation unit 30 is installed in the ultrasonic probe shown in FIG. 1, while the partition wall 50 as such is not installed in the ultrasonic probe shown in FIG. 6.

As described above, when the vent holes 60 configured to communicate air are formed at a portion of the housing 70 which covers the radiation unit 30, outside air may be drawn in to an interior of the housing 70 through the vent holes 60, and at this time, along with the inlet of the air, outside dust or foreign substance may be drawn in to the interior of the housing 70.

The inlet of the foreign substance or dust may negatively affect the printed circuit board and the electrical apparatus 110 provided at the interior of the ultrasonic probe, and may induce malfunctions of the ultrasonic probe.

Regarding the ultrasonic probe shown in FIG. 1, as the inletting of the dust or foreign substance being drawn in through the vent holes 60 into a space at which the electrical apparatus 110 is provided is physically blocked, the occurrence of the difficulty as such is prevented.

Regarding the ultrasonic probe shown on FIG. 6, the partition wall 50 shown in FIG. 1 is not present, and as the radiation unit 30, which is connected to the heat pipe 20, is installed so as to divide an inside space of the housing 70 of the ultrasonic probe, the radiation unit 30 is provided to perform the function of the partition wall 50 as well as the function of the radiation unit 30.

In particular, the radiation unit 30, in performing the function of the partition wall 50, is provided to block the space, at which the electrical apparatus 110 is provided, from an outside space that is being connected through the vent holes 60.

Thus, the movements of the dust or foreign substance, which may be drawn in through the vent holes 60 to a space at which the electrical apparatus 110 is situated, are physically blocked by the radiation unit 30.

As the radiation unit 30 is provided to separate a space at an interior of the housing 70 of the ultrasonic probe, the appropriate size of the radiation unit 30 should be manufactured or determined by considering the area of a cross section of an interior of the housing 70, and the shape of the radiation unit 30 should also be manufactured or determined by considering the area of a cross section of the interior of the housing 70.

The radiation unit 30 includes the plurality of radiation fins 31 which are provided with the shape of a panel that is formed with a metallic material, such as aluminum, such that the heat transferred via the heat pipe 20 may be scattered.

The condensation unit 22 of the heat pipe 20 is provided so as to make contact with respect to the plurality of radiation fins 31 of the radiation unit 30, and when the heat is released from the gas which is being moved to the condensation unit 22 as the gas is condensed at an inner wall of the condensation unit which is provided with a relatively lower temperature, the heat being released from the condensation unit 22 of the heat pipe 20 is scattered at the radiation fins 31.

Although not illustrated in the drawing, so as to additionally enhance the radiation performance, the radiation fin 40, which is configured to release the heat that is scattered from the radiation fins 31, may be adjacently provided with respect to the radiation unit 30.

As the cable extension unit 90 is provided at a central portion of the rear end of the ultrasonic probe on FIG. 6, the cable extension unit 90 may be eccentrically provided at the rear end of the ultrasonic probe so as to prevent the cable 80 from interfering with respect to the heat pipe 20 and the radiation unit 30.

In FIG. 1, the radiation fin 100 configured to release the heat being absorbed from the heat spreader 11 while being in contact with respect to the heat spreader 11 may be provided, so as to further enhance the radiation performance.

As illustrated in FIG. 1, the two units of the fin 100 may be adjacently provided with respect to an inner side surface of the housing 70, and the fin 100 may be formed with a metallic material having a relatively high heat conductivity, such as, for example, aluminum.

The fin 100 is configured to discharge the heat that is absorbed form the heat spreader 11 by means of heat conductivity via the housing 70.

FIG. 7 is provided to show an alternative exemplary embodiment of the ultrasonic probe shown in FIG. 6.

As shown in FIG. 7, the shape of the radiation unit 30, which is connected to the heat pipe 20 so as to scatter the heat that is transferred via the heat pipe 20, is provided to be different with respect to the radiation unit 30 shown in FIG. 6.

While the radiation unit 30 shown in FIG. 6 is structured with the plurality of radiation fins 31 having the shape of a panel while formed with a metallic material such as aluminum, the radiation unit 30 shown in FIG. 7 is provided with a shape which corresponds to the shape of the rear end of the housing 70 that corresponds to the radiation unit 30.

In particular, if the rear end of the housing 70 is provided with a shape of a semicircle that is convex with respect to the y-axis, the shape of the radiation unit 30 is formed with the shape of a semicircle that is convex with respect to the y-axis as well.

When the radiation unit 30 is formed as described above, the shape of the radiation unit 30 and the shape of the rear end of the housing 70 which covers the radiation unit 30 are identical with respect to each other, and thus the radiation unit 30 may be able to be installed at further adjacent position with respect to the housing 70.

When the radiation unit 30 is installed at a further adjacent position with respect to the housing 70, the gap between the radiation unit 30 and the housing 70 may be narrowed.

When the gap between the radiation unit 30 and the housing 70 is narrowed, the releasing of heat through the vent holes 60 may occur faster as compared to when the gap between the radiation unit 30 and the housing 70 is widened.

In addition, the radiation unit 30 illustrated in FIG. 7 is provided to perform the function of the partition wall 50, similarly as the radiation unit 30 illustrated in FIG. 6 is provided to perform the function of the partition wall 50.

As described above, when the vent holes 60 which are provided so as to communicate air are formed at the portion of the housing 70 which covers the radiation unit 30, outside air may be able to be drawn in to an interior of the housing 70 through the vent holes 60, and at this time, outside dust or foreign substance may also be drawn into the interior the housing 70 in conjunction with the inlet of the outside air. The inletting of the foreign substance or dust may negatively affect the electrical apparatus 110, such as, for example, a printed circuit board which is provided at an interior of the ultrasonic probe, and this may induce malfunctions of the ultrasonic probe.

Regarding the ultrasonic probe shown in FIG. 7, the partition wall 50 shown on FIG. 1 is not present, and as the radiation unit 30 connected to the heat pipe 20 is installed so as to divide an inside space of the housing 70 of the ultrasonic probe, the radiation unit 30 is provided to perform the function of the partition wall 50 as well as the function of the radiation unit 30. In particular, the radiation unit 30, with respect to its function as the partition wall 50, is provided to block the space at which the electrical apparatus 110 is provided from an outside space that is connected through the vent holes 60. Thus, the movements of the dust or foreign substance, which may be drawn in through the vent holes 60 to a space at which the electrical apparatus 110 is situated, are physically blocked by the radiation unit 30.

As the radiation unit 30 is provided to separate a space within the interior of the housing 70 of the ultrasonic probe, the size of the radiation unit 30 should be manufactured or determined by considering the area of a cross section of the interior of the housing 70, and the shape of the radiation unit 30 should also be manufactured or determined by considering the area of a cross section of the interior of the housing 70.

The radiation unit 30 may be formed with a metallic material, such as, for example, aluminum, so as to scatter the heat that is transferred via the heat pipe 20.

In FIG. 7, the cable extension unit 90 is provided at a central portion of the rear end of the ultrasonic probe, but the cable extension unit 90 may be eccentrically provided at the rear end of the ultrasonic probe such that the cable 80 may be prevented from interfering with respect to the heat pipe 20 and/or the radiation unit 30.

FIG. 8 is provided to show an alternative exemplary embodiment of the ultrasonic probe shown in FIG. 7.

As shown in FIG. 7, the shape of the radiation unit 30 shown in FIG. 8 is provided with a shape that corresponds to the shape of the rear end of the portion of the housing 70 which covers the radiation unit 30.

In particular, if the rear end of the housing 70 is provided with a shape of a semicircle that is convex with respect to the y-axis, the radiation unit 30 is formed with the shape of a semicircle that is convex with respect to the y-axis as well.

When the radiation unit 30 is formed as described above, the shape of the radiation unit 30 and the shape of the rear end of the portion of the housing 70 which covers the radiation unit 30 are identical with respect to each other, and thus the radiation unit 30 may be able to be installed in close correspondence with respect to the housing 70.

When the radiation unit 30 is installed at a closely corresponding adjacent position with respect to the housing 70, the gap between the radiation unit 30 and the housing 70 may be narrowed.

When the gap between the radiation unit 30 and the housing 70 is narrowed, in conjunction with the releasing of heat by use of the convection current of the air through the vent holes 60, the releasing of heat through heat conductivity may be considered as an effective method of releasing heat.

Thus, as illustrated in FIG. 8, the vent holes 60 are not formed at the rear end of the housing 70 adjacent to the radiation unit 30 so as to release heat through heat conductivity.

As described above, the radiation unit 30 is formed with a metallic material having relatively high heat conductivity such as aluminum, and thus heat is released to the exterior by use of heat conductivity via the housing 70, which has a lower heat conductivity with respect to the radiation unit 30.

In particular, because the heat conductivity of the radiation unit 30 is greater than the heat conductivity of the housing 70, and because the heat conductivity of the housing 70 is greater than the heat conductivity of outside air, the heat of the radiation unit 30 is transferred and released to the exterior of the housing 70 by means of heat conductivity through the housing 70.

When the vent holes 60 are not formed, the likelihood of dust or foreign substance being drawn in from outside through the vent holes 60 is reduced, and thus the size and/or the shape of the radiation unit 30 being designed to separate a space within the interior of the housing 70 is not necessarily required.

In FIG. 8, the vent holes 60 may be formed at the rear end of the housing 70 adjacent to the radiation unit 30. However, by having the gap between the vent holes 60 larger than the gap between the vent holes 60 as illustrated in FIG. 7, the vent holes 60 may be sparsely distributed.

In particular, by adding the releasing of heat through the convection current to the releasing of heat through heat conductivity, an increased effectiveness with respect to the releasing of heat may be induced. As described above, in a case when the vent holes 60 are sparsely distributed, the difficulty caused by an inlet of dust or foreign substance by the forming of the vent holes 60 may occur, and thus the radiation unit 30, similarly as the radiation unit 30 illustrated in FIG. 7, is provided to perform the functions of the partition wall 50. In particular, as the radiation unit 30 is required to separate a space within the interior of the housing 70 of the ultrasonic probe, the size of the radiation unit 30 should be manufactured or determined by considering the area of a cross section of an interior portion of the housing 70, and the shape of the radiation unit 30 should also be manufactured or determined by considering the area of a cross section of an interior portion of the housing 70.

In FIG. 8, the cable extension unit 90 is provided at a central portion of the rear end of the ultrasonic probe, but the cable extension unit 90 may be eccentrically provided at the rear end of the ultrasonic probe such that the cable 80 may be prevented from interfering with respect to the heat pipe 20 and/or the radiation unit 30.

In FIG. 9, a structure in accordance with another exemplary embodiment of the ultrasonic probe is schematically illustrated.

Referring to FIG. 9, the housing 70 of the ultrasonic probe includes a first housing 71 and a second housing 72, and the second housing 72 is formed with a metallic material having a relatively high heat conductivity, such as, for example, aluminum.

The heat pipe 20 is connected to the second housing 72, and the heat that is transferred through the heat pipe 20 after being absorbed at the heat spreader 11 is released to an outside through the second housing 72.

In particular, without separately having the radiation unit 30 installed in an interior of the housing 70 of the ultrasonic probe, the second housing 72, as a result of being formed with a metallic material having a relatively high heat conductivity, is provided to perform the function of the radiation unit 30.

When heat is transferred to the second housing 72, the heat is conducted and released to outside air which has relatively low heat conductivity, and thereby the heat radiation takes place.

Because the second housing 72 is provided to perform the function of the radiation unit 30, the vent holes 60 are not formed at the second housing 72 for effective heat radiation, and because the vent holes 60 are not formed, the partition wall 50 configured to separate the space in which the electrical apparatus 110 is provided is not installed as well.

Figure 10:
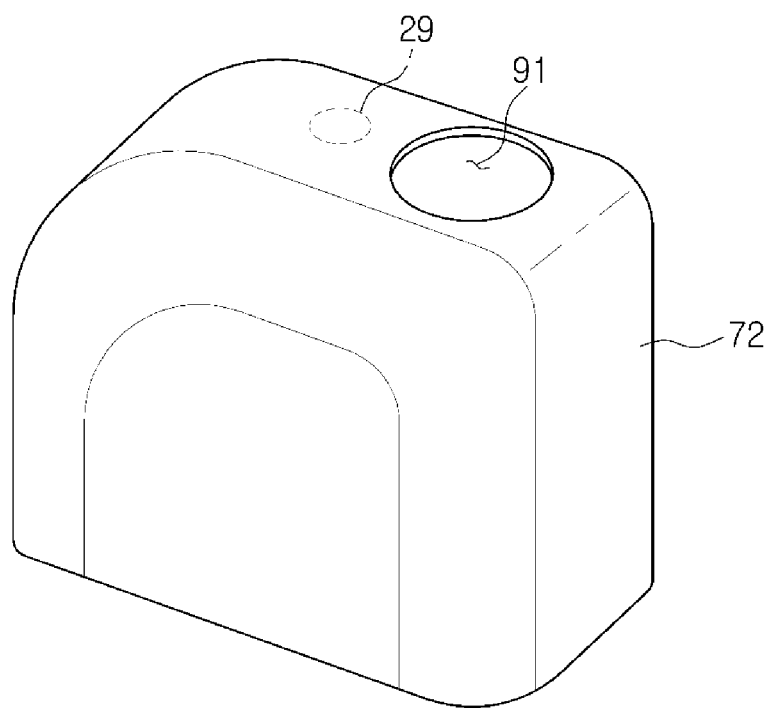
FIG. 10 is a perspective view illustrating a second housing of the ultrasonic probe of FIG. 9.

FIG. 10 is a perspective view separately illustrating only the second housing 72, which is configured to perform the function of the radiation unit 30 as described above.

A hole 91 at which the cable extension unit 90 is to be formed is eccentrically formed at a rear end of the second housing 72.

Then, a circle 29 illustrated in dotted line shows a portion to which the heat pipe 20 is to be connected.

The portion at which the cable extension unit 90 is formed is eccentrically provided so as to prevent the cable 80 from interfering with respect to the heat pipe 20.

In FIG. 9 as well, the cable extension unit 90 is eccentrically formed at the rear end of the second housing 72 of the ultrasonic probe.

As is apparent from the above, the heat stability of an ultrasonic probe can be enhanced by effectively releasing heat to an outside while the heat is generated by the ultrasonic probe.

Although a few exemplary embodiments have been shown and described, it will be appreciated by those skilled in the art that changes may be made in these exemplary embodiments without departing from the principles and spirit of the present inventive concept, the scope of which is defined in the claims and their equivalents.

What is claimed is:

1. An ultrasonic probe, comprising:
a housing;
a transducer configured to generate ultrasonic waves while disposed in an interior of the housing;
a heat pipe configured to facilitate a transfer of heat generated by the transducer;
a radiator connected to the heat pipe and configured to release the heat being transferred via the heat pipe to an exterior of the housing;
a partition wall which extends across an interior cross-section of the housing, contacts inner surfaces of the housing, and separates an inside space within the housing; and
an electrical apparatus provided in the interior of the housing,
wherein the heat pipe extends across the partition wall and the radiator is provided at a distal end of the heat pipe.

2. The ultrasonic probe of claim 1, further comprising:
a cable electrically connected to the electrical apparatus; and
a cable extender provided at a rear portion of the housing as to extend the cable to the exterior of the housing,
wherein the cable extender is positioned so as not to interfere with the radiator and so as not to interfere with the heat pipe.

3. The ultrasonic probe of claim 1, wherein:
the heat pipe is further configured to facilitate the transfer of the heat generated by the transducer in a first direction which differs from a radiation direction of the generated ultrasonic waves by at least 90 degrees.

4. The ultrasonic probe of claim 1, wherein:
a vent hole configured to facilitate a passage of air therethrough is provided at the housing and is further configured to cover the radiator.

5. The ultrasonic probe of claim 1, wherein:
the radiator comprises a radiation fin configured to scatter the heat transferred via the heat pipe.

6. The ultrasonic probe of claim 5, further comprising:
a radiation fan configured to release the heat scattered by the radiation fin to the exterior of the housing.

7. An ultrasonic probe, comprising:
a housing;
a transducer configured to generate ultrasonic waves while disposed in an interior of the housing;
a heat pipe configured to facilitate a transfer of heat generated by the transducer;
a radiator comprising a plurality of heat dissipating fins that is connected to the heat pipe and configured to release the heat being transferred via the heat pipe to an exterior of the housing; and
an electrical apparatus provided in the interior of the housing,
wherein the radiator extends across an interior cross-section of the housing and contacts inner surfaces of the housing such that an inside space within the housing is divided.

8. The ultrasonic probe of claim 7, wherein the radiator is positioned so as to isolate a space in which the electrical apparatus is provided.

9. The ultrasonic probe of claim 8, further comprising:
a cable electrically connected to the electrical apparatus; and
a cable extender provided at a rear portion of the housing as to extend the cable to the exterior of the housing,
wherein the cable extender is positioned so as not to interfere with the radiator and so as not to interfere with the heat pipe.

10. The ultrasonic probe of claim 7, wherein:
the radiator is provided with a shape thereof which corresponds to a shape of the housing.

11. The ultrasonic probe of claim 7, wherein:
the heat pipe is further configured to facilitate the transfer of the heat generated by the transducer in a first direction which differs from a radiation direction of the generated ultrasonic waves by at least 90 degrees.

12. The ultrasonic probe of claim 7, wherein:
a vent hole configured to facilitate a passage of air therethrough is provided at the housing and is further configured to cover the radiator.

13. The ultrasonic probe of claim 7, further comprising:
a radiation fan configured to release the heat scattered by the heat dissipating fins to the exterior of the housing.

14. An ultrasonic probe, comprising:
a housing;
a transducer configured to generate ultrasonic waves, the transducer being disposed inside the housing;
a heat pipe for facilitating a transfer of heat generated by the transducer;
a radiator connected to the heat pipe and configured to release the heat being transferred via the heat pipe to an exterior of the housing; and
a printed circuit board provided in an interior of the housing,
wherein the radiator is curved and extends across an interior cross-section of the housing.

15. A method for dispersing heat generated by an ultrasonic probe, the ultrasonic probe including a housing and a transducer configured to generate ultrasonic waves, and the method comprising:
positioning a heat pipe so as to facilitate a transfer of the heat generated by the ultrasonic probe;
connecting a radiator to the heat pipe so as to cause the heat generated by the ultrasonic probe to be transferred to an exterior of the housing; and
positioning a partition wall inside the ultrasonic probe such that the partition wall extends across an interior cross-section of the housing and contacts inner surfaces of the housing,
wherein the heat pipe is positioned so that it extends across the partition wall and the radiator is connected to a distal end of the heat pipe.

16. The method of claim 15, wherein the positioning the heat pipe further comprises positioning the heat pipe so as to facilitate the transfer of the heat generated by the ultrasonic probe in a first direction which differs from a radiation direction of the generated ultrasonic waves by at least 90 degrees.

17. The method of claim 15, wherein the radiator includes a radiation fin configured to scatter the heat transferred via the heat pipe.

18. The method of claim 17, wherein the radiator further includes a radiation fan, and wherein the connecting the radiator to the heat pipe further comprises positioning the radiation fan to facilitate a forcing of the scattered heat through the heat pipe toward the exterior of the housing.

* * * * *